(12) United States Patent
Upadhyay et al.

(10) Patent No.: US 6,251,383 B1
(45) Date of Patent: Jun. 26, 2001

(54) METHOD FOR EX-VIVO EXPANSION OF HEMATOPOIETIC CELLS

(75) Inventors: Shakti N. Upadhyay; Vikas Madan, both of New Delhi (IN)

(73) Assignee: National Institute of Immunology, New Delhi (IN)

( * ) Notice: Subject to any disclaimer, the term of this patent is extended or adjusted under 35 U.S.C. 154(b) by 0 days.

(21) Appl. No.: 09/339,759

(22) Filed: Jun. 24, 1999

(30) Foreign Application Priority Data

Apr. 20, 1999 (IN) ............................... 607/DEL/99

(51) Int. Cl.$^7$ .......................... A01N 63/00; A01N 65/00; A01N 37/18; C12Q 1/68; C12P 21/06
(52) U.S. Cl. .......................... 424/93.1; 424/195.1; 514/2; 435/6; 435/69.1; 435/325
(58) Field of Search ............................... 424/93.21, 93.1; 800/295, 278; 435/325, 455, 2; 536/23.1; 514/44

(56) References Cited

U.S. PATENT DOCUMENTS 5,683,698 * 11/1997 Chavali et al. .................. 424/195.1

OTHER PUBLICATIONS

Hungerford et al. Austrian Journal of Chemistry 51:1103–1111, 1998.*

Mathew et al. Fitoterapia 70:35–43, 1999.*

Bhattacharya et al. Indian Journal of Experimental Biology abstract, Oct. 1991.*

Yokozawa et al. Phytotherapy Research abstract, Feb. 2000.*

* cited by examiner

Primary Examiner—Karen M. Hauda
Assistant Examiner—Joseph Woitach
(74) Attorney, Agent, or Firm—Ladas and Parry

(57) ABSTRACT

A method for ex vivo expansion of the number of hematopoietic cells using a culture medium comprising an extract prepared from a plant of the Tinospora species and a method of ex vivo expansion of the number of hematopoietic cells by inducing IL-6 production by using a culture medium comprising an extract from a plant of the Tinospora species are described.

44 Claims, 3 Drawing Sheets

METHOD FOR EX-VIVO EXPANSION OF HEMATOPOIETIC CELLS

BACKGROUND OF THE INVENTION

Hematopoietic cell culture or ex vivo expansion of the number of hematopoietic cells is a rapidly growing area of tissue engineering with many potential applications in bone marrow transplantation, gene therapy and production of blood platelets etc. In recent years the number of allogenic bone marrow transplants have increased considerably as they have become a therapeutic option for hematologic, immunologic and malignant disorders. In addition, it has become a clinical practice to perform bone marrow transplants following chemotherapy and radiotherapy in cancer patients because chemotherapy and radiotherapy cause damage to the hematopoietic progenitors in the bone marrow and render the patient susceptible to infection.

At present the process of bone marrow transplantation is associated with various complications and discomfort. Bone marrow harvesting is painful and requires use of operating room procedures. Large numbers of cells are required for transplant and the early treatment relies on the infusion of a sufficient number of progenitor cells. Moreover compatible donors are in short supply. As a result, there has been much interest in the expansion of the number of bone marrow cells ex vivo prior to transplantation. Ex vivo expansion of hematopoietic cells has the potential to decrease the initial harvest necessary for successful engraftment. Through ex vivo cell expansion techniques, a small marrow specimen taken under local anaesthetic can be expanded into the large number of cells required for transplantation, thereby eliminating the large harvest procedure. Engraftment may be accelerated by increasing the number of progenitor and immature cells available for infusion. In addition, it may be possible to cryopreserve expanded cells to be infused at multiple time points, thereby allowing multiple cycles of chemotherapy. The use of expanded cells may also allow increased doses of chemotherapy thereby facilitating tumor reduction. More importantly, ex vivo expansion of the number of bone marrow cells has the potential for improving the transplant outcome by allowing clinicians to transplant more cells, to supplement transplants with mature progenitors to speed the recovery of neutrophils and platelets and to use a single hematopoietic harvest for repeated transplants over an extended period. Similar procedures could also be used for treatment of AIDs patients where HIV infected leukocytes could be eliminated by chemotherapy/radiotherapy and the autologous bone marrow cells expanded ex vivo could be transplanted back to restore the immunocompetence. The method for ex vivo expansion of the number of hemopoietic cells could also be used to generate activated and antigen sensitized immunocompetent cells for immunotherapy of cancer and infections. In addition, such methods may also be used for ex vivo expansion of genetically transfected or transformed hematopoietic cells for gene therapy.

The method of ex vivo expansion of the number of hematopoietic cells involves taking a small quantity of bone marrow or hematopoietic stem cells and producing more outside the body for later transplantation. Since the demonstration that direct contact between primitive hematopoietic cells and stroma is not required for long term in vitro hematopoiesis (Verfaillie, 1992) growth factors and cytokines have been used to substitute for the supportive function of the adherent layer (Zandstra et al. 1994). This has led to the development of methods for supporting bone marrow cell growth involving the use of cytokines, especially IL-6 and IL-3, and growth factors like stem cell factor (SCF) in the liquid media (Bernstein et al., 1991). IL-6 has been shown to act synergistically with IL-3 and SCF to augment the proliferation of human hematopoietic progenitor cells and to support colony formation from dormant murine hematopoietic progenitors (Ikebuchi et al., 1987: Koike et al.; 1988, Tanaka et al.; 1992). Cytokines and growth factors have been used both for static as well as perfusion cultures. Much greater expansion of the number of colony-forming cells is achieved in the presence of cytokines, IL-6 and IL-3 and SCF in perfusion bioreactor than in static culture (Koller et al.; 1993 a,b). Other culture systems used for the scale-up of marrow cultures include suspension, micro carriers, airlift and hollow fiber bioreactors.

Although there are various methods available for the ex vivo expansion of the number of cells using various combinations of cytokines or stromal cells, the magnitude of expanded progenitor cells that has been achieved, especially multi potential progenitors, is typically low. Moreover, the requirement for use of cytokines and growth factors whether natural or recombinant make the currently used methods very expensive and therefore more cost effective methods are needed urgently.

The method of ex vivo expansion of the number of hematopoietic cells described in this application, uses a water soluble plant extract prepared from a plant of the Tinospora species, belonging to family Menispermacease, preferably the plant is *Tinospora cordifolia*. Plants of the Tinospora species have been widely used in traditional Indian medicine for treatment of skin infections, arthritis, fever, dysentery, urinary tract infections, and diabetes (Gupta et al., 1967; Sharma and Sharma, 1981; Raghunathan and Sharma, 1969). *Tinospora cordifolia* has also been reported to protect mice against *E. coli* induced abdominal sepsis (Thatte et al., 1987, Thatte and Dahanukar, 1989). Crude preparations of *Tinospora cordofolia* have been used in the preparation of herbal formulations for treatment of skin diseases (Shah, U.S. Pat. No. 5,693,327, 1997), diabetes, (Dhaliwal, U.S. Pat. No. 5,886,029, 1997) and arthritis (Chavali et al., U.S. Pat. No. 5,683,698, 1997). None of these reports and patents suggest or describe the use of this plant material as in this invention.

SUMMARY OF THE INVENTION

The present invention describes a method for ex vivo expansion of the number of hematopoietic cells using a culture medium comprising an extract prepared from a plant of the Tinospora species. In one embodiment of the invention no exogenous cytokines and growth factors are added to the culture medium.

Another object of this invention is to provide a method of ex vivo expansion of the number of hematopoietic cells by inducing IL-6 production by using a culture medium comprising an extract prepared from a plant of the Tinospora species.

A further object of this invention relates to a method of production of IL-6 using stromal or endothelial cell culture.

Yet another object of this invention is a method for preparing a culture medium comprising an extract from a plant of the Tinospora species.

A yet further object of this invention is to prepare and use an extract from *Tinospora cordifolia*.

Another object of this invention is to provide a method for ex vivo expansion of the number of hematopoietic cells for various clinical applications like transplantation of ex vivo expanded hemopoietic cells for restoration of immunocompetence, generation of activated and antigen sensitized immunocompetent cells for immunotherapy of cancer and infections, and ex vivo expansion of genetically transfected or transformed hematopoietic cells for gene therapy.

DETAILED DESCRIPTION OF THE INVENTION

Figure 1:
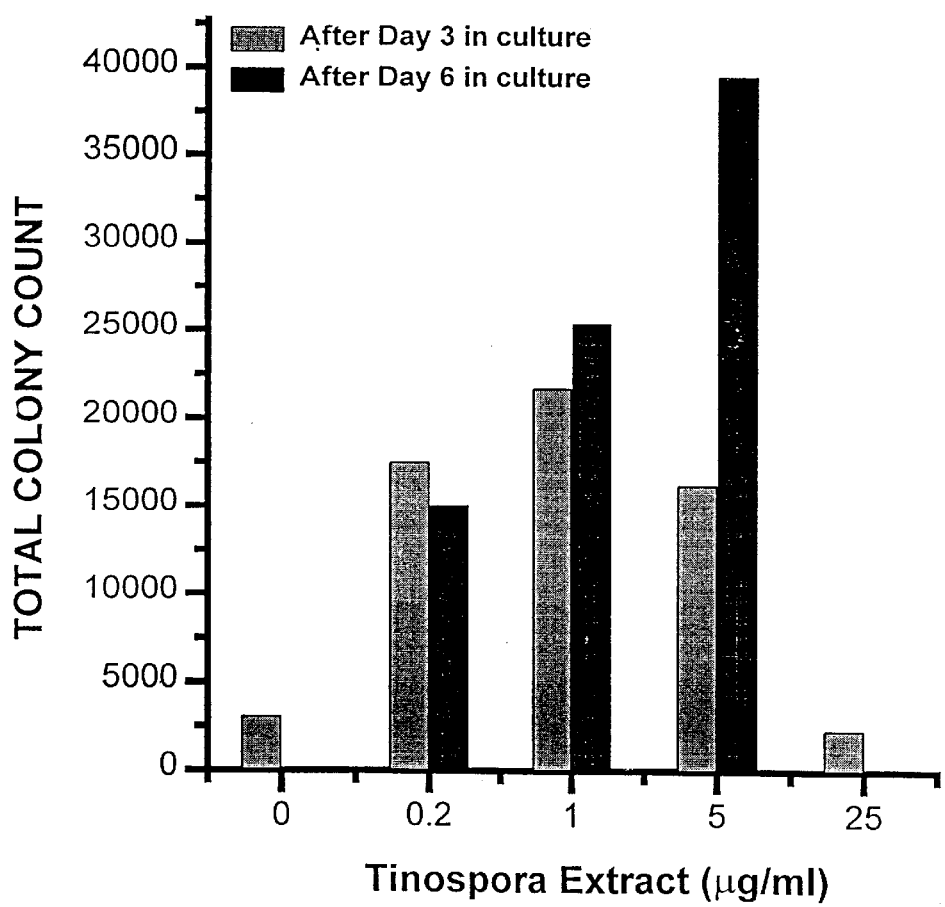
FIG. 1 represents the effect of Tinospora extract on the ex vivo propagation of hematopoietic cells using the colony assay.

The present invention provides a new composition which is culture medium comprising an extract prepared from a fresh or dried species of Tinospora, preferably from fresh or dried *Tinospora cordifolia*. The extract is a water soluble component which contains a protein conjugated with one or more carbohydrate groups. The extract can also include free carbohydrates (polysaccharides) and proteins. The proteins may include all types of proteins, examples of which are simple or conjugated proteins such as lipoproteins, glycoproteins and metalloproteins.

Types of proteins conjugated with one or more carbohydrate groups are glycoproteins, proteoglycans and glycopeptides. Glycoproteins are any class of conjugated protein such as a compound of a protein and a carbohydrate group. Proteoglycans are glycoproteins containing a high content of carbohydrates. Glycopeptides are any class of peptides that contain carbohydrates.

Use of this plant extract in the culture medium induces expansion of the number of multi-potential hematopoietic cells including stem, progenitor and/or clonogenic cells. The hematopoietic cells comprise multipotential stem cells, immunocompotent cells and stromal cells including fibroblast and endothelial cells. The hematopoietic cells used for expansion by this method can be obtained from a patient or donor bone marrow sample or from bone marrow samples procured from a bank or from hemopoietic cells obtained from umbilical cord or peripheral blood. The hematopoietic cells can also be genetically transfected or transformed.

Gene transfection involves introduction of corrective or protective genes into the hematopoietic stem cells using various vector systems like a retroviral vector. Stem cells being the progenitor, subsequent generations of immunocomptent cells would carry such genes and the expression of such genes would have the desired effect. For example, introduction of drug resistant genes into the hematopoietic stem cells could protect the subsequent generations of immune cells against toxic effects of chemotherapy in cancer patients, or in case of an inherited genetic defect such as chronic granulomatus disease where mutation of the gene for NADPH oxidase, responsible for generation of superoxide ion, leads to inability of phagocyctic cells to kill bacteria and introduction of this gene into hematopoietic stem cells could allow the subsequent generations of phagocyctic cells to regain their ability to defend against such infections.

This approach, referred to as gene therapy, is being proposed for a variety of disease conditions. One of the requirements of this therapeutic strategy is that the number of genetically transfected or transformed cells need to be expanded or multiplied in vitro, and the expression of the gene must be selected for before it can be used in patients for the desired therapeutic effect. The method described in this patients application allows for expansion of such genetically transfected or transformed hematopoietic stem cells, ex-vivo or in vitro.

Addition of the water soluble extract from a plant of the Tinospora species to the culture medium eliminates the need to use exogenous cytokines such as recombinant cytokines and growth factors thus making it a very cost effective method for ex vivo expansion of the number of hematopoietic cells.

Although no cytokines are required, this plant extract can be combined with cytokines like IL-3, GM-CSF or soluble receptor for IL-6 (sIL-6R) and/or growth factors like SCF and/or any other hematopoiesis promoting agents such as those from natural products for synergistic effect.

This invention further demonstrates that a water soluble extract from a plant of the Tinospora species induces production of IL-6 and thus provides the stimulus for hematopoiesis under ex vivo culture conditions. The method can also be used for production of IL-6 from genetically engineered hematopoietic cells, cord endothelial cells, or stromal cells.

The method described in this invention can be used in static or perfusion cultures using bioreactors. It can also be used as culture medium with micro carriers, airlift and hollow fiber bioreactors.

Extracts can be prepared as follows:

Fresh or dried parts of a plant of a Tinospora species are ground and soaked in water at room temperature for 1–72 hours or longer. The supernatant is filtered. The supernatant can then be used, concentrated or lyophilized or set aside for later use. To prepare an extract containing purified total protein (a mixture of proteins which includes proteins conjugated with carbohydrates) salt is added to the supernatant after filtering. A precipitate is formed and this can be dialyzed to remove the salt and this extract can be used, concentrated or lyophilized or set aside for further use. The supernatant or the extract can also be passed over a lectin column to isolate glycoproteins.

Preferably the Tinospora species that is used is *Tinospora cordofolia*.

Preferably the stems of the plant are used.

The dose of extract used is based on its protein content. The extract is used at a protein concentration of 0.1–100 µg/ml of the culture medium, preferably 1–10 µg/ml of the culture medium.

The methods described herein are demonstrated by the following examples which should not be construed as limiting the scope of this invention.

1. Method of preparation of Tinospora extract for use in the hematopoietic cell culture medium:

The Tinospora extract for use in the hematopoietic cell culture medium is prepared by any of the following methods:

Method 1: Fresh or dried parts of *Tinospora cordifolia*, preferably the stems are ground and soaked in water for 1–72 hours or longer, preferably 24–48 hours, at room temperature. The supernatant is filtered and the protein content is estimated. The filtered supernatant can be used as is or it may be concentrated or lyophilized or set aside for further use.

Method 2: Fresh or dried parts of *Tinospora cordifolia* preferably the stems are ground and soaked in water for 1–72 hours or longer, preferably 24–48 hours, at room temperature. The supernatant is filtered and is subjected to ammonium sulphate (up to 90% saturation) precipitation and the precipitate thus obtained is resuspended in phosphate buffered saline (PBS) (0.1M and pH 7.2–7.4). The solution thus obtained is dialysed against PBS for 24–48 hours at 4° C. or at room temperature to remove the salts and this protein rich fraction can be used as such or concentrated or lypholized or set aside for later use.

Method 3: Fresh or dried parts of *Tinospora cordifolia* preferably the stems are ground and soaked in water at room temperature for 1–72 hours or longer, preferably 24–48 hours. The supernatant is filtered and is subjected to ammonium sulphate (up to 90% saturation) precipitation and the precipitate thus obtained is resuspended in phosphate buffered saline (PBS). (0.1 M and pH 7.2–7.4). The solution thus obtained is dialyzed against PBS for 24–48 hours at 4° C. or at room temperature to remove the salts. The protein rich fraction is then passed over the lectin column (Concanavalin A immobilized on 4% beaded agarose). Glycoproteins adsorbed on the column are then eluted using a Tris buffer (10 mM pH 7.4) containing 0.2M glucose. The preparation containing total glycoproteins thus obtained can be used as such or concentrated or lypholized to be used at a later time.

Method 4. Fresh or dried parts of *Tinospora cordifolia* preferably the stems are ground and soaked in water at room temperature for 1–72 hours or longer, preferably 24–48 hours. The supernatant is filtered and is directly passed over a lectin column (Concanavalin A immobilized on 4% beaded agarose). Glycoproteins thus adsorbed on the column are then eluted using a Tris buffer (10 mM pH 7.4) containing 0.2M glucose. The preparation containing total glycoproteins thus obtained can be used as such or concentrated or lypholized to be used at a later time.

Although the Tinospora extract prepared as described above in Methods 1–4 are stable even at room/ambient temperature, preservatives and/or antibiotics can be added for long term preservation. This preparation can also be stored at 4° C. or frozen below 0° C. for long term storage.

2. Preparation of culture medium comprising Tinospora extract:

To prepare the culture medium for hematopoietic cells ex vivo, Tinospora extract can be mixed with or added to any cell/tissue culture medium of choice. The medium used in this study was Iscove's Modified Dulbecco's Medium (IMDM) supplemented with 20% (v/v) fetal bovine serum (FBS). The medium was prepared by dissolving 17.7 gm IMDM, 3.024 gm sodium bicarbonate in 800 mL Milli-Q water. The solution was filter sterilized using 0.22 $\mu$m filter and incubated at room temperature for 2 days to check sterility. In the sterile medium Gentamycin and amphotericin B were added at final concentrations of 50 $\mu$g/mL and 0.5 $\mu$g/mL, respectively. The amount of the Tinospora extract added in the culture medium was quantified on the basis of its total protein concentration and the amount of protein added ranged from 0.1 $\mu$g–100 $\mu$g/ml of the culture medium, preferably between 1–10 $\mu$g/ml of the culture medium.

3. Experimental data on the use of culture medium comprising Tinospora extract for ex vivo expansion of hematopoietic cells:

EXPERIMENTAL PROCEDURES AND RESULTS

A) Isolation of Bone Marrow Cells

Isolation of bone marrow cells was performed under sterile conditions in a laminar flow hood. Inbred DBA/2J mice were sacrificed by cervical dislocation and the femurs were dissected out. The bones were cleansed by scraping off muscles and cartilage. The bone marrow cells were flushed using a 26 g needle with medium containing 2.5% fetal bovine serum (FBS) and collected in a sterile tube. Single cell suspensions were prepared by repeated passage through 21 g needle. Viable cells were counted using Trypan blue exclusion principle.

B) Setting up of Stromal Layer

For preparing the stromal layer, the cells of two femurs were directly flushed in a T-25 culture flask. The cells were allowed to adhere and spread for about 8–10 days, after which the medium was changed. This depleted the non-adherent cell population. The stromal layer attained confluency in another 5–7 days. At this stage, the stroma was subcultured into culture plates.

C) Subculture of Stromal Layer

Spent media was pipetted off from the flask when a confluent stromal layer was formed. The cells were washed twice with PBS. The cells were then treated with dispase enzyme solution and incubated at 37° C. 1 mL of dispase stock (2.5 Units/ml) was used for a confluent flask (25 cm$^2$). After incubation for 20–40 minutes, when the majority of cells had rounded off and started detaching from the surface, the enzyme was diluted with 1 mL of 0.5% (w/v) solution of bovine serum albumin (BSA) in PBS. The cells were then dislodged using a 1 ml hypodermic syringe and 21 g needle. The cell suspension was collected in IMDM media containing 5% FBS. Cells were pelleted down at 1000 rpm for 8–10 minutes and resuspended in medium. Cells were counted and plated in 35 mm culture plates at a cell density of 0.7–1×10$^6$ viable cells/plate. Plates were incubated at 33° or 37° C. in 5% $CO_2$ incubator. Cells were allowed to adhere and spread for a period of 1–2 days.

D) Irradiation of Stromal Layer

The multiplication of stromal cells was arrested, without affecting their supportive role in hematopoiesis, by irradiation with y-rays. The cells were irradiated with a dose of 1500 rads.

E) Initiation and Maintenance of Long-term Hematopoietic Culture DBA/2J mice were sacrificed and single bone marrow cell suspension was obtained. 2×10$^6$ viable bone marrow cells were overlaid on irradiated preformed stromal cells in 35 mm culture plates in a culture media comprising Tinospora extract. After 3–7 days half of the culture medium was replaced with fresh medium comprising Tinospora extract. Following this the culture dishes were fed with replacement of half of the medium comprising Tinospora extract every 3rd day.

F) Colony Assay

Cultures were terminated on various days of culture; after pipetting out the spent medium, the cells were washed twice with PBS. The cells were treated with 250 $\mu$L of dispase stock solution (2.5 U/mL) at 37° C. for 20–25 minutes. The enzyme was then diluted with the addition of 200 $\mu$L of 0.5% (w/v) solution of BSA in PBS. Cells were dislodged using a 21 g needle and transferred to a sterile tube containing media. Plates were washed once with media and cells were pooled into the tube. Dislodged cells were centrifuged at 1000 rpm for 8–10 minutes. Cells were resuspended in media and viable cell number was enumerated. The cells were then suspended in methyl cellulose media at the density of 10,000 cells/mL in a tube. The suspension was vortexed and the tube was allowed to stand for 10 minutes for the air bubbles to escape. Media was dispensed in wells of 24 well plate in triplicate (300 $\mu$L per well) with the help of a syringe using 16 g blunt end needle. A uniform layer of the semi-solid medium was made by gentle rotation of plate. Spaces between the wells were filled with sterile water to maintain absolute humidity during culture. The plates were incubated for a period of 14 days at 33° or 37° C. in a 5% $CO_2$ incubator. Criteria of 50 or more cells for hematopoietic colonies was followed. Total number of colonies were counted. The results show that Tinospora extract enhances the production of colonies. The number of colonies is almost 15–20 times that of the control was noted in cultures incubated for 6 days with medium comprising 5 µg/ml of Tinospora extract (FIG. 1).

G) Cell Proliferation Assay

Figure 2:
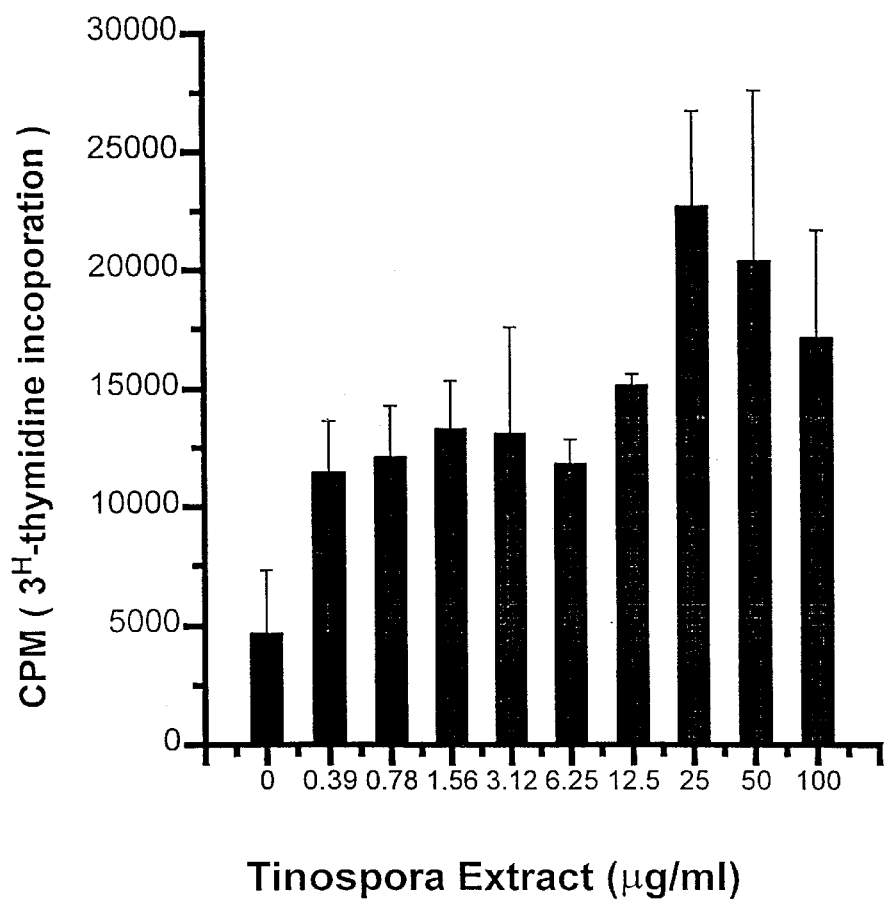
FIG. 2 represents the effect of Tinospora extract on the ex vivo proliferation of hematopoietic cells using 3H-thymidine incorporation assay.

Total bone marrow cells obtained as described in A. were plated in 96 well plate at a concentration of $0.5 \times 10^6$ cells/well. These cells were incubated with different concentrations (0.4–100 µg/ml of protein concentration) of Tinospora extract in triplicates, for 48 hours at 37° C. and 5% $CO_2$. $^3$H-thymidine (0.5 uCi/well) was added to the culture and the plates were further incubated overnight. Cells were harvested and incorporation of $^3$H-thymidine was counted using beta counter. The results showed *Tinospora cordifolia* extract induced dose dependent increase in proliferation of bone marrow hematopoietic cells (FIG. 2).

H) Estimation of IL-6 Production

Figure 3:
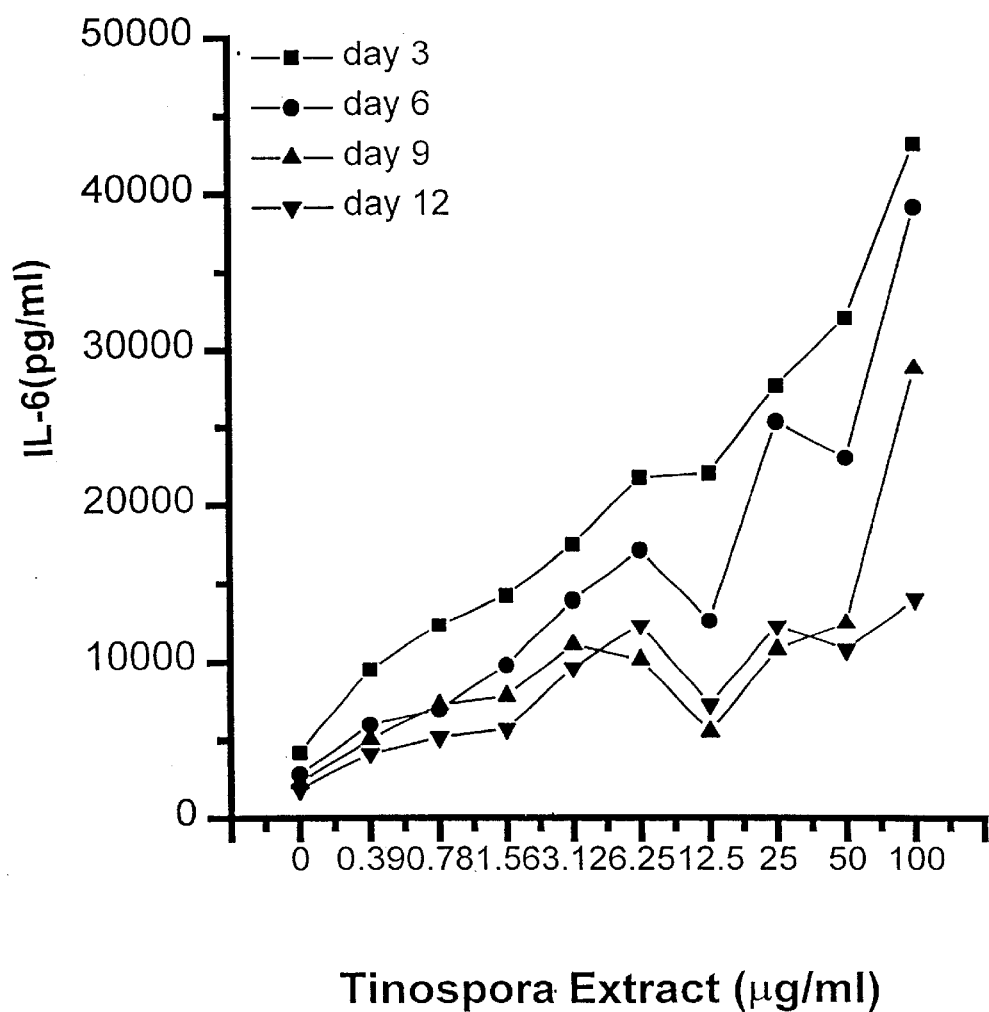
FIG. 3 represents the effect of Tinospora extract on the production of IL-6 by hematopoietic cells, ex vivo, as measured by ELISA.

Stromal cells as described in B were plated in 35 mm culture plates and incubated with different concentrations (0.4–100 ug/ml of protein concentration) of Tinospora extracts. Culture supernatants were collected on days 3, 6, 9 and 12, aliquoted and stored at −70° C. until further use. IL-6 was estimated by ELISA using commercially available kits. Results show that Tinospora extract at all doses induces production of IL-6, the maximum production is attained on day 3 with a medium comprising 100 ug/ml (protein concentration) of Tinospora extract (FIG. 3).

REFERENCES

Bernstein ID, Andrew R G, Zsebo K M (1991) Blood, 77:2316–232.1
Chavali et al., (1997) U.S. Pat. No. 5,683,698.
Gupta et al., (1967) Ind.J. Med. Res., 66:733–745.
Dhaliwal, K. S. (1999) U.S. Pat. No. 5,886,029.
Ikebuchi, K., Wong, G. G., Clark, S. C., Ihle, J. N., Hirai. Y., Ogawa, M. (1987) Proc. Nat'l. Acad. Sc. USA 84, 90-35-9039.
Koike et al., (1988) Exp. Med., 168:879–890.
Koller, M. R, Bender, J. G., Miller, W. M., Papoutsakis, E. T. (1993a) Biotechnology II, 358–372.
Koller, M. R., Emerson, S. G., Palsson, B. O. (1993b). Blood 82, 378–384.
Sharma and Sharma (1981) Ind. J. Pharnacol., 13:96–97, 1981.
Raghunathan and Sharma (1969) J. Res. Ind. Med., 4:59–62, 1969.
Shah, E (1997) U.S. Pat. No. 5,693,327.
Tanaka et al., (1992) Blood, 80:1743–1749.
Thatte et al. (1987) Indian Drugs, 25:95–97, 1987.
Thatte U and Dahanukar S. (1989) Phytotherapy Res., 3:43–49, 1989.
Verfaillie, C. M. (1992) Blood 79, 2821–2826.
Zandstra, P. W., Eaves, C. J. and Piret, J. M. (1994) Biotechnology 12, 909–914.

What is claimed is:

1. An in-vitro method for for increasing the number of hematopoietic cells comprising culturing the cells in a medium, said medium comprising a water soluble extract prepared from a plant *Tinospora cordifolia* said extract present in an amount effective to increase the number of said cells.

2. The method according to claim 1, wherein the extract comprises glycoproteins, glycopeptides or proteoglycans.

3. The method according to claim 1, wherein the extract is used at a protein concentration of 0.1–100 ug/ml of the medium.

4. The method according to claim 1, wherein the hematopoietic cells are obtained from bone marrow, umbilical cord blood or peripheral blood of a mammal.

5. The method according to claim 4, wherein the mammal is a human.

6. The method according to claim 1, wherein the hematopoietic cells comprise multipotential stem cells, stromal cells, fibroblasts or endothelial cells.

7. The method according to claim 6, wherein the stromal cells, or endothelial cells, or cell lines derived therefrom are obtained from bone marrow, umbilical cord blood or peripheral blood of a mammal.

8. The method according to claim 1, wherein the hematopoietic cells used in the method were genetically transfected or transformed prior to culturing the cells.

9. The method according to claim 1, wherein the extract is prepared by soaking fresh or dried parts of the plant of *Tinosnora cordifolia* in water for at least 1 hour and filtering the solution.

10. The method according to claim 9, wherein the filtered system is precipitated using a salt, the precipitate is dissolved in a buffer to form a solution, the solution is dialyzed to remove the salt and the solution is passed over a lectin column wherein the filtered solution bound to the lectin column is eluted.

11. The method according to claim 9, wherein the filtered system is passed over a lectin column wherein the filtered solution bound to the lectin column is eluted.

12. An in-vitro method for increasing the number of hematopoietic cells comprising culturing the cells in a medium, without exogenous cytokines and growth factors said medium comprising a water soluble extract prepared from a plant *Tinospora cordifolia*, said extract present in an amount effective to expand stem, progenitor and clonogenic cells.

13. The method according to claim 12, wherein the extract comprises glycoproteins, glycopeptides or proteoglycans.

14. The method according to claim 12, wherein the extract is used at a protein concentration of 0.1–100 ug/ml of the medium.

15. The method according to claim 12, wherein the hematopoietic cells are obtained from bone marrow, umbilical cord blood or peripheral blood of a mammal.

16. The method according to claim 15, wherein the mammal is a human.

17. The method according to claim 12, wherein the hematopoietic cells comprise multipotential stem cells, stromal cells, fibroblasts or endothelial cells.

18. The method according to claim 12, wherein the stromal cells, or endothelial cells, or cell lines derived therefrom are obtained from bone marrow, umbilical cord blood or peripheral blood of a mammal.

19. The method according to claim 12, wherein the hematopoietic cells used in the method were genetically transfected or transformed prior to culturing the cells.

20. The method according to claim 12, wherein the extract is prepared by soaking fresh or dried parts of the plant of *Tinospora cordifolia* in water for at least 1 hour and filtering the solution.

21. The method according to claim 20, wherein the filtered system is precipated using a salt, the precipitate is dissolved in a buffer to form a solution, the solution is dialyzed to remove the salt and the solution is passed over a lectin column and the adsorbed material is eluted.

22. The method according to claim 20, wherein the filtered system is passed over a lectin column and the absorbed material is eluted.

23. A method for inducing the production of IL-6 by hematopoietic cells comprising culturing the cells in a medium said medium comprising a water soluble extract prepared from a plant of *Tinospora cordifolia* said extract present in an amount effective to induce IL-6 production.

24. The method according to claim 23, wherein the extract comprises glycoproteins, glycopeptides or proteoglycans.

25. The method according to claim 23, wherein the extract is used at a protein concentration of 0.1–100 ug/ml of the medium.

26. The method according to claim 23, wherein the hematopoietic cells are obtained from bone marrow, umbilical cord blood or peripheral blood of a mammal.

27. The method according to claim 26, wherein the mammal is a human.

28. The method according to claim 23, wherein the hematopoietic cells comprise multipotential stem cells, stromal cells, fibroblasts or endothelial cells.

29. The method according to claim 28 wherein the stromal cells, or endothelial cells or cell lines derived therefrom are obtained from bone marrow or umbilical cord blood.

30. The method according to claim 23, wherein the hematopoietic cells used in the method were genetically transfected or transformed prior to culturing the cells.

31. A method according to claim 23, wherein the method is used for large scale production of IL-6.

32. The method according to claim 23, wherein the extract is prepared by soaking fresh or dried parts of the plant of *Tinospora cordifolia* in water for at least 1 hour and filtering the solution.

33. The method according to claim 32, wherein the filtrate is precipated using a salt, the precipitate is dissolved in a buffer to form a solution, the solution is dialyzed to remove the salt and the solution is passed over a lectin column and the adsorbed material is eluted.

34. The method according to claim 32, wherein the filtrate is passed over a lectin column and the adsorbed material is eluted.

35. An improved method for transplantation of hematopoietic cells into a mammal comprising culturing isolated hematopoietic cells in a medium and transplanting said hematopoietic cells into said mammal, wherein the improvement comprises culturing in vitro the hematopoietic cells in a medium comprising a water soluble extract prepared from a plant *Tinospora cordifolia*, said extract present in an amount effective to increase the number of said hematopoietic cells, and transplanting said increased number of hematopoietic cells into a mammal.

36. The method according to claim 35 wherein the mammal is a human.

37. The method according to claim 35, wherein the extract comprises glycoproteins glycopeptides or proteoglycans.

38. The method according to claim 35, wherein the extract is used at a protein concentration of 0.1–100 ug/ml of the medium.

39. The method according to claim 35, wherein the hematopoietic cells are obtained from bone marrow, umbilical cord blood or peripheral blood of the mammal.

40. The method according to claim 35, wherein the hematopoietic cells comprise multipotential stem cells, stromal cells, fibroblast cells or endothelial cells.

41. The method according to claim 40, wherein the stromal cells, or endothelial cells, or cell lines derived therefrom are obtained from bone marrow, umbilical cord blood or peripheral blood of a mammal.

42. The method according to claim 35, wherein the extract is prepared by soaking fresh or dried parts of the plant of *Tinospora cordifolia* in water for at least 1 hour and filtering the solution.

43. The method according to claim 42, wherein the filtered solution is precipitated using a salt, the precipitate is dissolved in a buffer to form a solution, the solution is dialyzed to remove the salt and the solution is passed over a lectin column wherein the filtered solution bound to the lectin column is eluted.

44. The method according to claim 42, wherein the filtered solution is passed over a lectin column wherein the filtered solution bound to the lectin column is eluted.

* * * * *